US009309304B2

(12) United States Patent
Bourne et al.

(10) Patent No.: US 9,309,304 B2
(45) Date of Patent: Apr. 12, 2016

(54) GLYCATION CROSS-LINK BREAKERS TO INCREASE RESISTANCE TO ENZYMATIC DEGRADATION

(71) Applicants: NEW YORK SOCIETY FOR THE RUPTURED AND CRIPPLED MAINTAINING THE HOSPITAL FOR SPECIAL SURGERY, New York, NY (US); Cornell University, Ithaca, NY (US)

(72) Inventors: Jonathan W. Bourne, Fairport, NY (US); Peter A. Torzilli, Ridgefield, CT (US)

(73) Assignees: CORNELL UNIVERSITY, Ithaca, NY (US); NEW YORK SOCIETY FOR THE RUPTURED AND CRIPPLED MAINTAINING THE HOSPITAL FOR SPECIAL SURGERY, New York, NY (US)

( * ) Notice: Subject to any disclaimer, the term of this patent is extended or adjusted under 35 U.S.C. 154(b) by 190 days.

(21) Appl. No.: 13/895,527

(22) Filed: May 16, 2013

(65) Prior Publication Data
US 2013/0310539 A1 Nov. 21, 2013

Related U.S. Application Data

(60) Provisional application No. 61/647,774, filed on May 16, 2012.

(51) Int. Cl.
*A61K 38/39* (2006.01)
*A61K 8/91* (2006.01)
*C07K 14/78* (2006.01)
*A61K 38/00* (2006.01)

(52) U.S. Cl.
CPC ...................... *C07K 14/78* (2013.01)

(58) Field of Classification Search
None
See application file for complete search history.

(56) References Cited

U.S. PATENT DOCUMENTS

| | | | | |
|---|---|---|---|---|
| 4,879,135 | A * | 11/1989 | Greco et al. | 623/1.48 |
| 5,584,875 | A * | 12/1996 | Duhamel | A61F 2/06 |
| | | | | 427/2.25 |
| 8,053,449 | B2 * | 11/2011 | Fabricant | 514/332 |
| 2002/0037496 | A1 | 3/2002 | Jacobson et al. | 435/4 |
| 2005/0187609 | A1 * | 8/2005 | Brar et al. | 623/1.15 |
| 2007/0162124 | A1 * | 7/2007 | Whittaker | 623/13.14 |
| 2009/0297581 | A1 * | 12/2009 | Atanasoska et al. | 424/423 |
| 2010/0015206 | A1 * | 1/2010 | Flanagan et al. | 424/426 |
| 2010/0331760 | A1 * | 12/2010 | Atanasoska et al. | 604/20 |
| 2011/0008397 | A1 * | 1/2011 | Cohen | A61L 27/38 |
| | | | | 424/400 |
| 2014/0030308 | A1 * | 1/2014 | Crohn | 424/423 |

OTHER PUBLICATIONS

Aldini et al. (2013) Molecular strategies to prevent, inhibit, and degrade advanced glycoxidation and advanced lipoxidation end products, Free Rad. Res., vol. 47 (Suppl.1), pp. 93-137.*
Yeni, Yener N. "Novel in Vitro Modification of Bone for an Allograft with Improved Toughness Osteoconductivity." Henry Ford Health System, Report Date: Oct. 2013.
Aronson, D. "Cross-Linking of Glycated Collagen in the Pathogenesis of Arterial and Myocardial Stiffening of Aging and Diabetes." [In Eng]. J Hypertens 21:1 (2003): 3-12.
Bai, P., K. Phua, T. Hardt, M. Cernadas, and B. Brodsky. "Glycation Alters Collagen Fibril Organization." [In Eng]. Connect Tissue Res 28:1-2 (1992): 1-12.
Bailey, A. J., R. G. Paul, and L. Knott. "Mechanisms of Maturation and Ageing of Collagen." [In Eng]. Mech Ageing Dev 106: 1-2 (1998): 1-56.
Bank, R. A., J. M. TeKoppele, G. Oostingh, B. L. Hazleman, and G. P. Riley. "Lysylhydroxylation and Non-Reducible Crosslinking of Human Supraspinatus Tendon Collagen: Changes with Age and in Chronic Rotator Cuff Tendinitis." [In Eng]. Ann Rheum Dis 58:1 (999): 35-41.
Bourne, J. W., and P. A. Torzilli. "Molecular Simulations Predict Novel Collagen Conformations During Cross-Link Loading." [In Eng]. Matrix Biol 30:5-6 (2011): 356-60.
Buehler, M. J. "Atomistic and Continuum Modeling of Mechanical Properties of Collagen: Elasticity, Fracture, and Self-Assembly." [In Eng]. Journal of Materials Research 21:8 (2006): 1947-61.
Camp, R. J., M. Liles, J. Beale, N. Saeidi, B. P. Flynn, E. Moore, S. K. Murthy, and J. W. Roberti. "Molecular Mechanochemistry: Low Force Switch Slows Enzymatic Cleavage of Human Type I Collagen Monomer." [In Eng]. J Am Chem Soc 133:11 (2011); 4073-78.
Chen, A. C., M. M. Temple, D. M. Ng, N. Verzijl, J. DeGroot, J. M. TeKoppele, and R. L. Sah. "Induction of Advanced Glycation End Products and Alterations of the Tensile Properties of Articular Cartilage." [In Eng]. Arthritis Rheum 46;12 (2002): 3212-7.
Cheng, G., L. L. Wang, L. Long, H. Y. Liu, H. Cui, W. S. Qu, and S. Li, "Beneficial Effects of C36, a Novel Breaker of Advanced Glycation Endproducts Cross-Links, on the Cardiovascular System of Diabetic Rats." [In Eng]. Br J Pharmacol 152:8 (2007): 1196-206.

(Continued)

*Primary Examiner* — Manjunath Rao
*Assistant Examiner* — Samuel Liu
(74) *Attorney, Agent, or Firm* — Leason Ellis LLP

(57) ABSTRACT

The present invention relates to a method to treat a grafts, implant, scaffold, and constructs, including allografts, xenografts, autografts, and prosthetics comprising collagen, with an inhibitor of collagen cross-links and/or advanced glycation endproducts (AGE), in order to alleviate the mechanical weakness induced by the cross-links. The invention also provides for kits for use in the operating theater during autograft, allograft or xenograft procedures, or for preparing allograft, xenografts or prosthetics that have not been already treated prior to packaging. The kit comprises a first agent or agents that inhibit collagen cross-links and/or advanced glycation endproducts, instructions for use, optionally a wash or rinse agent, and a device for containing the graft and first agent.

10 Claims, 5 Drawing Sheets

(56) References Cited

OTHER PUBLICATIONS

Cheng, G., L. L. Wang, W. S. Qu, L. Long, H. Cui, H. Y. Liu, Y. L. Cao, and S. Li. "C16, a Novel Advanced Glycation Endproduct Breaker, Restores Cardiovascular Dysfunction in Experimental Diabetic Rats." [In Eng]. Acta Pharmacol Sin 26:12 (2005): 1460-6.

Choudhary, M. I., G. Abbas, S. Ali, S. Shuja, N. Khalid, K. M. Khan, Rahman Atta ur, and F. Z. Basha. "Substituted Benzenediol Schiff Bases as Promising New Anti-Glycation Agents." [In Eng]. J Enzyme Inhib Med Chem 26:1 (2011): 98-103.

Freemont, A. J., and J. A. Hoyland. "Morphology, Mechanisms and Pathology of Musculoskeletal Ageing." [In Eng]. J Pathol 211:2 (2007): 252-9.

Gautieri, Alfonso, Markus J. Buehler, and Alberto Redaelli. "Deformation Rate Controls Elasticity and Unfolding Pathway of Single Tropocollagen Molecules." Journal of the Mechanical Behavior of Biomedical Materials 2:2 (2009): 130-37.

Huang, C., and I. V. Yannas. "Mechanochemical Studies of Enzymatic Degradation of Insoluble Collagen Fibers." [In Eng]. J Biomed Mater Res 11:1 (1977): 137-54.

In 't Veld, P., and M. J. Stevens. "Simulation of the Mechanical Strength of a Single Collagen Molecule." [In Eng]. Biophys J 95:1 (2008): 33-39.

Joshi, D., R. Gupta, A. Dubey, A. Shiwalkar, P. Pathak, R. C. Gupta, V. Chauthaiwale, and C. Dutt. "Trc4186, a Novel Age-Breaker, Improves Diabetic Cardiomyopathy and Nephropathy in Ob-Zsfl Model of Type 2 Diabetes." [In Eng]. J Cardiovasc Pharmacol 54:1 (2009): 72-81.

Kuznetsova, N. V., McBride, D. J. and Leikin, S. "Changes in thermal stability and microunfolding pattern of collagen helix resulting from the loss of alpha2(I) chain in osteogenesis imperfecta murine." J Mol Biol 331 (2003): 191-200.

Maroudas, A., G. Palla, and E. Gilav. "Racemization of Aspartic Acid in Human Articular Cartilage." [In Eng]. Connect Tissue Res 28:3 (1992): 161-9.

Motwani, J. G., and E. J. Topol. "Aortocoronary Saphenous Vein Graft Disease: Pathogenesis, Predisposition, and Prevention." [In Eng]. Circulation 97: 9 (1998): 916-31.

Nabeshima, Y., E. S. Grood, A. Sakurai, and J. H. Herman. "Uniaxial Tension Inhibits Tendon Collagen Degradation by Collagenase in Vitro." [In Eng]. J Orthop Res 14:1 (1996): 123-30.

Ottani, V., D. Martini, M. Franchi, A. Ruggeri, and M. Raspanti. "Hierarchical Structures in Fibrillar Collagens." [In Eng]. Micron 33:7-8 (2002): 587-96.

Paik, D. C., L. Y. Saito, D. D. Sugirtharaj, and J. W. Holmes. "Nitrite-Induced Cross-Linking Alters Remodeling and Mechanical Properties of Collagenous Engineered Tissues." [In Eng]. Connect Tissue Res 47: 3 (2006): 163-76.

Pathak, P., R. Gupta, A. Chaudhari, A. Shiwalkar, A. Dubey, A. B. Mandhare, R. C. Gupta, D. Joshi, and V. Chauthaiwale. "Trc4149 a Novel Advanced Glycation End Product Breaker Improves Hemodynamic Status in Diabetic Spontaneously Hypertensive Rats." [In Eng]. Eur J Med Res 13:8 (2008): 388-98.

Purslow, P. P., T. J. Wess, and D. W. Hukins. "Collagen Orientation and Molecular Spacing During Creep and Stress-Relaxation in Soft Connective Tissues." [In Eng]. J Exp Biol 201:1 (1998): 135-42.

Puxkandl, R., I. Zizak, O. Paris, J. Keckes, W. Tesch, S. Bernstorff, P. Purslow, and P. Fratzl. "Viscoelastic Properties of Collagen: Synchrotron Radiation Investigations and Structural Model." [In Eng]. Philos Trans R Soc Land B Biol Sci 357:1418 (2002): 191-7.

Rahbar, S., and. J. L. Figarola. "Novel Inhibitors of Advanced Glycation Endproducts." [In Eng]. Arch Biochem Biophys 419:1 (2003): 63-79.

Reddy, G. K. "Glucose-Mediated in Vitro Glycation Modulates Biomechanical Integrity of the Soft Tissues but Not Hard Tissues." [In Eng]. J Orthop Res 21:4 (2003): 738-43.

Reddy, G. K., L, Stehno-Bittel, and C. S. Enwemeka. "Glycation-Induced Matrix Stability in the Rabbit Achilles Tendon." [In Eng]. Arch Biochem Biophys 399:2 (2002): 174-80.

Ruberti, J. W., and N. J. Hallab. "Strain-Controlled Enzymatic Cleavage of Collagen in Loaded Matrix." [In Eng]. Biochem Biophys Res Commun 336:2 (2005): 483-9.

Sasaki, N. A., M. C. Garcia-Alvarez, Q. Wang, L. Ermolenko, G. Franck, N. Nhiri, M. T. Martin, N. Audic, and P. Potier. "N-Terminal 2,3-Diaminopropionic Acid (Dap) Peptides as Efficient Methylglyoxal Scavengers to Inhibit Advanced Glycation Endproduct (Age) Formation." [In Eng]. Bioorg Med Chem 17:6 (2009): 2310-20.

Sell, D. R., and V. M. Monnier. "Conversion of Arginine into Ornithine by Advanced Glycation in Senescent Human Collagen and Lens Crystallins." [In Eng]. J Biol Chem 279:52 (2004): 54173-84.

Tanaka, S., G. Avigad, E. F. Eikenberry, and B. Brodsky. "Isolation and Partial Characterization of Collagen Chains Dimerized by Sugar-Derived Cross-Links." [In Eng]. J Biol Chem 263:33 (1988): 17650-7.

Tang, Yuye, Roberto Ballarini, Markus J. Buehler, and Steven J. Eppell. "Deformation Micromechanisms of Collagen Fibrils under Uniaxial Tension." Journal of The Royal Society Interface 7:46 (2010): 839-50.

Verzijl, N., J. DeGroot, Z. C. Ben, O. Brau-Benjamin, A. Maroudas, R. A. Bank, J. Mizrahi, et al. "Crosslinking by Advanced Glycation End Products Increases the Stiffness of the Collagen Network in Human Articular Cartilage: A Possible Mechanism through Which Age is a Risk Factor for Osteoarthritis." [In Eng]. Arthritis Rheum 46:1 (2002): 114-23.

Verzijl, N., J. DeGroot, E. Oldehinkel, R. A. Bank, S. R. Thorpe, J. W. Baynes, M. T. Bayliss, et al. "Age-Related Accumulation of Maillard Reaction Products in Human Articular Cartilage Collagen." [In Eng]. Biochem J 350: 2 (2000): 381-7.

Verzijl, N., J. DeGroot, S. R. Thorpe, R. A. Bank, J. N. Shaw, T. J. Lyons, J. W. Bijlsma, et al. "Effect of Collagen Turnover on the Accumulation of Advanced Glycation End Products." [In Eng]. J Biol Chem 275:50 (2000): 39027-31.

Wyatt, K. E., J. W. Bourne, and P. A. Torzilli. "Deformation-Dependent Enzyme Mechanokinetic Cleavage of Type I Collagen." [In Eng]. J Biomech Eng 131:5 (2009): 051004.

Zareian, R., K. P. Church, N. Saeidi, B. P. Flynn, J. W. Beale, and J. W. Ruberti. "Probing Collagen/Enzyme Mechanochemistry in Native Tissue with Dynamic, Enzyme-Induced Creep." [In Eng]. Langmuir 26:12 (2010): 9917-26.

\* cited by examiner

A:

B:

GLYCATION CROSS-LINK BREAKERS TO INCREASE RESISTANCE TO ENZYMATIC DEGRADATION

CROSS REFERENCE TO RELATED APPLICATION

The present application claims priority to U.S. Patent Application Ser. No. 61/647,774, filed May 16, 2012, which is hereby incorporated by reference in its entirety.

GOVERNMENT FUNDING

This invention was made with Government support under Grant Number NIH-NCRR TL1RR024998 awarded by the National Institutes of Health. The United States Government has certain rights in the invention.

FIELD OF THE INVENTION

This invention relates to a method to treat grafts, implants, scaffolds or constructs that contain collagen, at least in a portion of the graft, implant, scaffold or construct, including allografts, xenografts, autografts, and prosthetics, with a modifier, reducer, and/or inhibitor of the cross-linking of collagen and/or age glycation endproducts (AGE) in order to alleviate the mechanical weakness, increased enzymatic degradation, and failure of the implants, that can be induced by collagen and AGE crosslinks.

The invention also relates to kits for use in the operating theater during autograft, allograft or xenograft procedures, or for preparing allograft, xenografts or prosthetics, that have not been already treated prior to packaging comprising at least one collagen cross-linking and/or AGE inhibitor, instructions for use, and optionally at least one wash and/or rinse agent, and a device for holding the graft, implant, scaffold or construct and the cross-linking inhibitor.

BACKGROUND OF THE INVENTION

Fibrillar collagens are structural proteins that assemble into a complex ordered structure of molecules cross-linked together to form an interconnected supramolecular fibril structure (Ottani et al. 2002). Collagens contribute to the mechanical properties of almost all tissues throughout the body including skin, tendon, ligament, bone, and cartilage (Bailey, Paul, and Knott 1998; Ottani et al. 2002).

Collagen is highly resistant to enzymatic breakdown, but is susceptible to a small number of specialized collagenolytic enzymes or collagenases. In part due to this resistance to enzymatic cleavage, collagen has a very slow turnover rate in many tissues of the body. The half-life for collagen has been reported on the order of decades in healthy tissues (Verzijl, DeGroot, Thorpe et al. 2000; Maroudas, Palla, and Gilav 1992; Bank et al. 1999). Due to the long protein half-life in vivo, collagen is one of the proteins that undergo spontaneous glycation and the formation of measurable amounts of Advanced Glycation Endproducts (AGEs) during aging (Choudhary et al. 2011; Sell and Monnier 2004; Verzijl, DeGroot, Oldehinkel et al. 2000; Verzijl, DeGroot, Thorpe et al. 2000).

Glycation, also called non-enzymatic glycosylation, is a spontaneous, non-enzymatic process in which a reducing sugar, such as glucose or fructose, reacts with a free amino group (e.g. lysine or arginine) to form a reactive Schiff base. The Schiff base then rearranges to form an Amadori product which undergoes further reactions, collectively known as a Maillard reaction, to form AGEs (Aronson 2003; Bailey, Paul, and Knott 1998). Of interest is that these reactions can result in stable covalent cross-links between two amine groups of amino acids, such as lysine or arginine (Bailey, Paul, and Knott 1998; Sell and Monnier 2004; Verzijl et al. 2002).

AGE accumulation in soft tissues is a function of tissue aging and accelerated by diabetes due to hyperglycemia (Bai et al. 1992; Freemont and Hoyland 2007; Reddy 2003; Reddy, Stehno-Bittel, and Enwemeka 2002). AGE cross-linking results in changes in the mechanical properties of soft tissues, which include increased Young's modulus, maximum failure load, stress, and toughness, as well as decreased elongation and strain, while in mineralized tissue there are minimal changes in these properties after glycation (Reddy 2003; Reddy, Stehno-Bittel, and Enwemeka 2000). In addition, AGE cross-linking has been implicated in a variety of pathological aging-related changes, including vascular (Aronson 2003), and articular cartilage stiffening (Chen et al. 2002; Verzijl, DeGroot, Oldehinkel et al. 2000), which may contribute to arteriosclerosis and osteoarthritis, respectively.

Computational molecular modeling was previously performed using steered molecular dynamics to simulate mechanical loading of a covalently cross-linked collagen (Bourne and Torzilli 2011). These loading conditions approximated mechanical force transmitted through covalent intermolecular cross-links, such as those caused by AGEs. Computational results predicted that force transmitted via cross-links would result in local disruption and micro-unfolding of the collagen triple helix at approximately 350 pN (minor micro-unfolding) and 900 pN (major micro-unfolding) (Bourne and Torzilli 2011). These values are well below those previously described as causing collagen failure (Bourne and Torzilli 2011; Buehler 2006; Tang et al. 2010).

Based upon molecular modeling and the experimental results set forth herein, it has been shown that mechanical forces on cross-linked collagen substrates would accelerate enzyme degradation, and that it would be desirable to decrease or eliminate these cross-links, such as those caused by AGE, prior to implantation of grafts, implants, scaffolds, or constructs into a subject.

SUMMARY OF THE INVENTION

This invention is based upon the novel and surprising discovery that combining glycation cross-linking with mechanical loading (each of which individually protects collagen from enzymatic degradation) causes accelerated enzymatic degradation. More importantly, and not obvious from previous reports on AGE cross-links and enzymatic degradation, is that the combined data indicate that removing or modifying cross-links in tissues that are mechanically loaded is a method to better protect or stabilize collagenous tissues.

Thus, these scientific results and molecular modeling data lead to the conclusion that the removal of cross-links in collagenous tissues that are then loaded mechanically in vivo improves tissue survival.

Based upon these finding, one embodiment of the present invention is a method of modifying, reducing, inhibiting and/or eliminating cross-links in collagen in a graft, implant, scaffold or construct suitable for implantation into a subject for the treatment, repair or replacement of defects or injury in biological tissue or an organ, by contacting or incubating the graft, implant, scaffold or construct with an agent that modifies, reduces, inhibits and/or eliminates cross-links in collagen for a time and at a temperature in which the cross-links in collagen are modified, reduced, inhibited and/or eliminated, prior to implantation of the graft, implant, scaffold or construct into the subject.

Another embodiment of the present invention is a method of modifying, reducing, inhibiting and/or eliminating advance glycation endproducts in a graft, implant, scaffold or construct suitable for implantation into a subject for the treatment, repair or replacement of defects or injury in biological tissue or an organ by contacting or incubating the graft, implant, scaffold or construct with an agent that modifies, reduces, inhibits and/or eliminates advance glycation endproducts for a time and at a temperature in which the advance glycation endproducts are modified, reduced, inhibited and/or eliminated, prior to implantation of the graft, implant, scaffold or construct into the subject.

A further embodiment of the present invention is a method of modifying, reducing, inhibiting and/or eliminating cross-links in collagen in a graft, implant, scaffold or construct suitable for implantation into a subject for the monitoring and/or facilitating the function of a biological tissue or organ, by contacting or incubating the graft, implant, scaffold or construct with an agent that modifies, reduces, inhibits and/or eliminates cross-links in collagen for a time and at a temperature in which the cross-links in collagen are modified, reduced, inhibited and/or eliminated, prior to implantation of the graft, implant, scaffold or construct into the subject.

A further embodiment of the present invention is a method of modifying, reducing, inhibiting and/or eliminating advance glycation endproducts in a graft, implant, scaffold or construct suitable for implantation into a subject for the monitoring and/or facilitating the function of a biological tissue or organ, by contacting or incubating the graft, implant, scaffold or construct with an agent that modifies, reduces, inhibits and/or eliminates advance glycation endproducts for a time and at a temperature in which the advance glycation endproducts are modified, reduced, inhibited and/or eliminated, prior to implantation of the graft, implant, scaffold or construct into the subject.

Additionally, these methods could comprise a further step of washing and/or rinsing the agent that inhibits the collagen cross-linking or the AGE from the graft, implant, scaffold or construct, prior to implantation of the graft, implant, scaffold or construct, into the subject.

It is further contemplated that these methods of the present invention will be added to the protocols already in place for processing grafts, implants, scaffolds, and constructs regardless of the source, i.e., natural or synthetic.

While the method can be used on grafts, implants, scaffolds, and constructs implanted into any subject, mammals are preferred, and humans are most preferred.

The biological tissue that is in need of treatment, repair or replacement includes, but is not limited to; musculoskeletal, including bone, tendon, ligaments, cartilage and the discs of the spine; vascular, including but not limited to, arteries, vessels, and heart valves; epidermal and dermal; connective tissue, including but not limited to, subcutaneous tissue; neurological and the associated dura tissue surrounding the brain and spinal cord; and dental.

Additionally, organs that are in need of treatment, repair or replacement include, but are not limited to, bone, skin, heart, lung, esophagus, kidney, liver, and lymph glands.

The biological tissue that is in need of monitoring and/or facilitating includes, but is not limited to; musculoskeletal, including bone, tendon, ligaments, cartilage and the discs of the spine; vascular, including but not limited to, arteries, vessels, and heart valves; epidermal and dermal; connective tissue, including but not limited to, subcutaneous tissue; neurological and the associated dura tissue surrounding the brain and spinal cord; and dental.

Additionally, organs that are in need of monitoring and/or facilitating include, but are not limited to, bone, skin, heart, lung, esophagus, kidney, liver, and lymph glands.

Grafts, implants, scaffolds, and constructs that can be contacted with the agent include autografts, isografts, allografts, xenografts, and prosthetics.

Yet a further embodiment of the present invention is a kit comprising one or more first agents that reduces or eliminates cross-links in collagen, instructions for use of such agents, one or more second agents for washing and/or rinsing the first agents from the graft, implant, scaffold or construct, and one or more devices that serve to contain the grafts and agents, and can provide mechanical perturbation and/or maintain the graft in a specific shape. This kit could be used in a production facility prior to the graft, implant, scaffold or construct being packaged for sale, or in a hospital setting after a graft has been harvested from an individual for further implantation.

A further embodiment of the present invention is a kit comprising one or more first agents that reduces or eliminates advance glycation endproducts, instructions for use of such agents, and one or more second agents for washing and/or rinsing the first agents from the graft, implant, scaffold or construct, and one or more devices that serve to contain the grafts and agents, and can provide mechanical perturbation and/or maintain the graft in a specific shape. This kit could be used in a production facility prior to the graft, implant, scaffold or construct being packaged for sale, or in a hospital setting after a graft has been harvested from an individual for further implantation.

BRIEF DESCRIPTION OF THE DRAWINGS

For the purpose of illustrating the invention, there are depicted in drawings certain embodiments of the invention. However, the invention is not limited to the precise arrangements and instrumentalities of the embodiments depicted in the drawings.

FIG. 4A shows results of the 3-day and 7-day cross-linked fibers. FIG. 4B shows results of the 7-Day cross-linked fibers only.

DETAILED DESCRIPTION OF THE INVENTION

Figure 1:
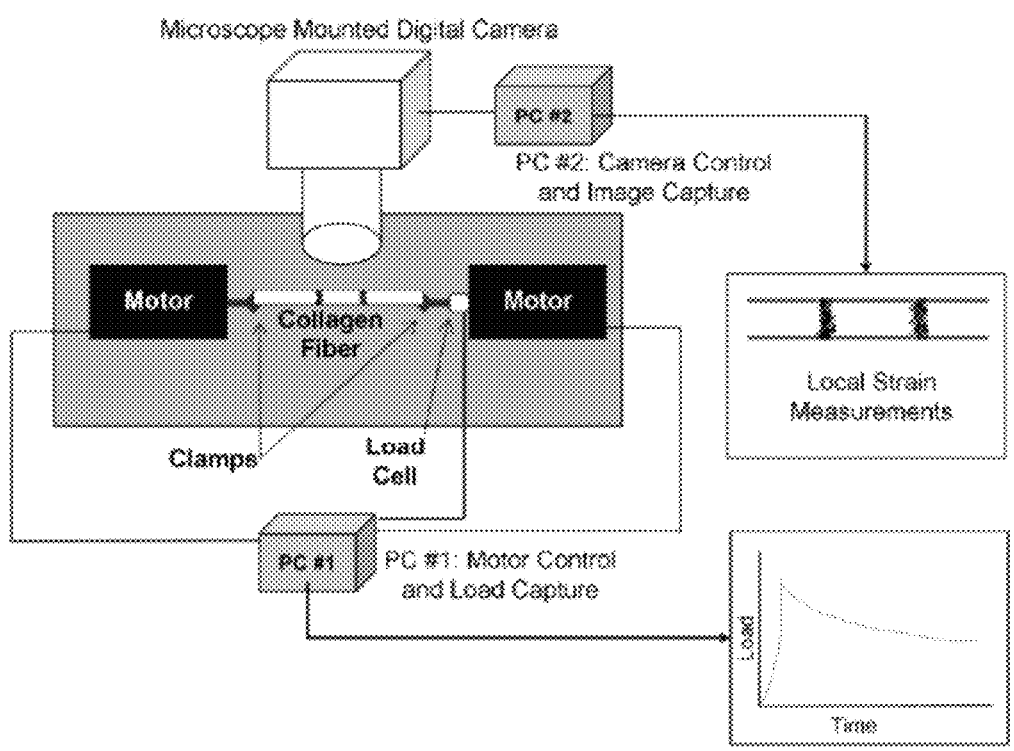
FIG. 1 is a schematic of Collagen Enzyme Mechano-Kinetic Automated Test System (CEMKATS).

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense, and the scope of the present invention is defined by the appended claims.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

DEFINITIONS

The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term.

The terms "graft", "implant", "construct", and "scaffold" are used interchangeably throughout this application and means any material implanted, inserted or grafted into the body that maintains support and tissue contour.

The term "subject" as used in this application means an animal with an immune system such as avians and mammals Mammals include canines, felines, rodents, bovines, equines, porcines, ovines, and primates. Avians include, but are not limited to, fowls, songbirds, and raptors. Thus, the invention can be used in veterinary medicine, e.g., to treat companion animals, farm animals, laboratory animals in zoological parks, and animals in the wild. The invention is particularly desirable for human medical applications.

The terms "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

The terms "treat", "treatment", and the like refer to a means to slow down, relieve, ameliorate or alleviate at least one of the symptoms of the defect or injury or reverse the defect or injury after its onset.

The term "repair" and the like refer to a means to fix, or put in good condition, or restore to working condition a defect or injury.

The terms "replace", "replacement", and the like refer to a means to substitute or take the place of defective or injured tissue.

The term "biocompatible" as used in the application means capable of coexistence with living tissues or organisms without causing harm.

The term "agent" as used herein means a substance that produces or is capable of producing an effect and would include, but is not limited to, chemicals, pharmaceuticals, biologics, small molecules, antibodies, nucleic acids, peptides, and proteins. In some embodiments of the present invention, the effect that the agent would produce is the modifying, reducing, inhibiting and/or eliminating advance glycation endproducts and/or collagen cross-links.

The term "portion" as used herein means a part, section, or quantity within a larger whole.

The term "enzyme mechano-kinetic effect", "EMK effect" or "EMK" as used herein refers to changes in rates of enzymatic degradation of collagen by degrading enzymes, which was first described in by Wyatt, Bourne, and Torzilli 2009.

Collagen AGE Cross-Linking

As discussed above, glycation, also called non-enzymatic glycosylation, is a spontaneous, non-enzymatic process which forms AGEs. AGE accumulation in soft tissues is a function of tissue aging, is also accelerated by diabetes due to hyperglycemia, and results in changes that have been implicated in a variety of age-related pathologies.

Also as discussed above, computational molecular modeling has shown that mechanical force transmitted through intermolecular cross-links, like AGEs, result in collagen degradation at much lower forces than previously thought (Bourne and Torzilli 2011).

Based upon these molecular modeling results, it was hypothesized and conceived that mechanical forces on cross-linked collagen substrates could paradoxically accelerate enzyme degradation. This hypothesis was tested by cross-linking a collagen substrate, i.e., tendon tissue, and then measuring the rate of enzymatic degradation as a function of applied mechanical deformation, i.e., applied strain, and found to be correct.

Thus, based upon the results set forth herein that show mechanical forces on cross-linked collagen substrates accelerate enzyme degradation, it would be desirable to decrease or eliminate these cross-links in collagen, such as those caused by AGE. This would be desirable in grafts prior to implantation.

Simulation of Collagen AGE Cross-Linking

A major source of collagen intermolecular cross-links during aging are attributed to AGEs, which result in age associated accumulation of collagen structural changes including fluorescent adducts and covalent sugar based cross-links (Bailey, Paul, and Knott 1998; Sell and Monnier 2004; Verzijl et al. 2002).

In the study set forth herein, ribose was used to cross-link collagen as it is a well characterized reactive sugar model that exhibits a faster reaction rate than glucose, while yielding identical end products to those formed with glucose (Tanaka et al. 1988; Bai et al. 1992; Reddy, Stehno-Bittel, and Enwemeka 2002).

3-day and 7-day incubation times with 0.2 M ribose were used based on published glycation kinetic data, where incubation of 2-4 days was sufficient to cause measurable differences in fluorescence and collagen solubility due to AGE formation (Tanaka et al. 1988; Bai et al. 1992). In addition, 7-days of ribose exposure appeared to effectively saturate the ultrastructural, fluorescent, and mechanical properties of rat tail tendon (Bai et al. 1992).

Figure 2:
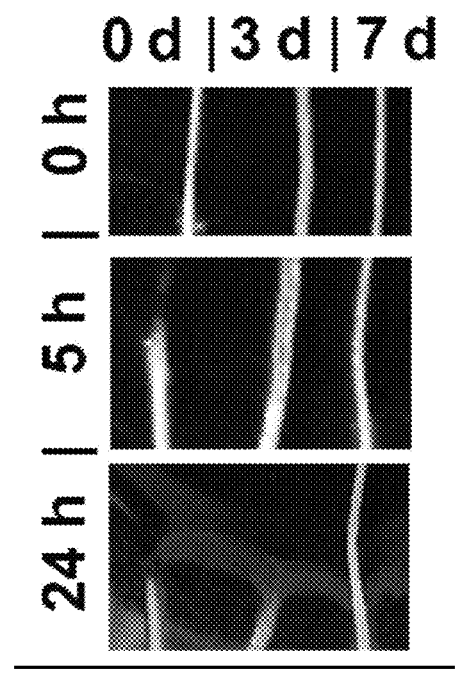
FIG. 2 are images from an unloaded fiber enzyme susceptibility test. Fibers of comparable size from the same rat tail were treated with 0.2 M ribose for 0 ("0 d"), 3 ("3 d") or 7 ("7 d") days and then exposed to a 1% collagenase solution at room temperature. Representative images at the air—collagenase interface of the fibers were digitally recorded at the 0 hours (start) and after 5 and 24 hours of collagenase exposure.

As was previously reported, accumulation of collagen cross-links results in increased resistance to collagenolytic digestion (Verzijl, DeGroot, Oldenhinkel et al. 2000; Verzijl et al. 2002; Paik et al. 2006). In agreement with these previous reports that cross-linking is protective, the results of the unloaded enzyme susceptibility test showed decreased susceptibility to collagenase as cross-linking duration increased from 3 to 7 days (Example 2; FIG. 2).

Collagen Tensile Strain at Equilibrium

Figure 3:
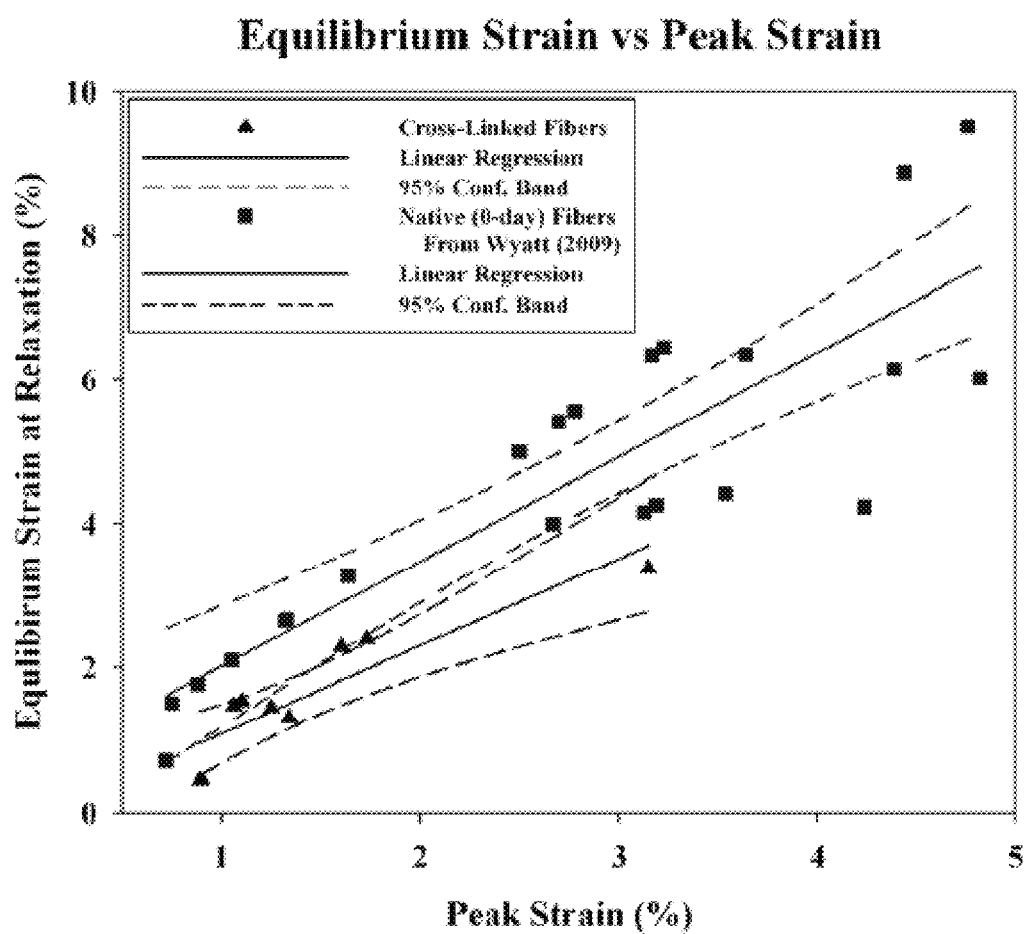
FIG. 3 depicts a graph of equilibrium strain versus peak strain from the mechanical relaxation tests for the glycation cross-linked fibers (triangles) as compared to historical data for native fibers (squares) from a previous study (Wyatt et al. 2009).

Previous mechanical tests using untreated native rat tail tendons showed a relaxed to peak tensile strain ratio ($\epsilon_r/\epsilon_p$) after stress relaxation of approximately 1.71±0.37 ($\epsilon_r/\epsilon_p$, mean±standard deviation, n=23), indicating that the strain increased during relaxation by 71% (Wyatt, Bourne, and Torzilli 2009). Cross-linking appears to attenuate this tensile strain increase during relaxation, as a smaller relaxed-to-peak tensile strain ratio of 1.25±0.21 was observed ($\epsilon_r/\epsilon_p$, n=5) in the 7-day fibers (Example 3; FIG. 3).

A regression analysis was performed for the native and cross-linked fibers using a linear (straight-line) fit to the equilibrium vs. peak strain data (SigmaPlot 10, Systat Software, Inc., Chicago, Ill.). The slope of the mean regression line for the native fibers was 1.45±0.88 (r=0.865, n=23) and was different from unity (p=0.022) (Wyatt, Bourne, and Torzilli 2009). The slope of cross-linked fibers was 1.21±0.64 (mean±standard deviation, r=0.907, n=9), and was not statistically different from unity (i.e., peak=equilibrium, p>0.350). However the two slopes could not be statistically distinguished from each other (p=0.461) (Example 3; FIG. 3).

This result was attributed to several factors. The range of the applied peak strains in this study were smaller than those used in the previous study by Wyatt, Bourne and Torzilli, especially the 3-day fibers which were only deformed between 0.89-1.25% tensile strain in this study. Further, the 3-day fibers that were combined with the 7-day fibers were likely not completely cross-linked and represented an intermediate state between native and 7-day fibers (Example 3; FIG. 3).

Taken together these data suggest that the cross-linking causes the tendon microfiber mechanical relaxation response to behave closer to a viscoelastic material in which the applied peak strain does not change during stress relaxation ($\epsilon_r/\epsilon_p$ ratio of unity). These results are in agreement with Purslow et al., where it was also found strain increases during stress relaxation which appeared to be due, at least in part, to structural rearrangements that were restricted by the collagen-collagen intermolecular cross-links (Purslow, Wess, and Hukins 1998).

Collagen "Protective Effect" Paradox

Several studies reported that mechanical force applied to collagenous substrates inhibits degradation by bacterial collagenase (Huang and Yannas 1977; Nabeshima et al. 1996; Ruberti and Hallab 2005; Wyatt, Bourne, and Torzilli 2009; Zareian et al. 2010). Nabeshima et al. discounted enzyme inhibition as a result of restricted enzyme diffusion effects while Wyatt et al. discounted inhibition by pH or osmotic effects (Nabeshima et al. 1996; Wyatt, Bourne, and Torzilli 2009). In combination with results from a recent study using full length parallel single collagen molecules exposed to bacterial collagenase (Camp et al. 2011), these data suggest that inhibition can be attributed to mechanical force-deformation effects at the protein level. Molecular modeling studies have described a range of protein conformational changes due to tensile mechanical force, including helical unwinding (Gautieri, Buehler, and Redaelli 2009; Veld and Stevens 2008), all of which indicate that the mechanical force results in collagenase inhibition through a mechanics-induced protein conformational effect.

Due to the hierarchical structure of collagen within the extracellular matrix of tissues, tensile forces applied at the macro and micro scales are transmitted via intermolecular cross-links (Puxkandl et al. 2002). At the molecular level (nano scale) this results in forces being transmitted across the amino acid side chains that form bridging intramolecular cross-links (Tang et al. 2010). Recent molecular modeling results now indicate that the transmission of tensile load via these cross-links can cause disruption and micro-unfolding of the triple helix and that these micro-unfolding events occur at force levels (<1,000 pN) below previously reported damage mechanisms (Bourne and Torzilli 2011).

As discussed above and shown in Examples 1-4, when tendon microfibers were treated with ribose to add glycation cross-links through AGEs, and then exposed to bacterial collagenase degradation, the unloaded fiber digestion tests showed that the 7-day cross-linked fibers are highly resistant to enzymatic degradation. However, when cross-linked fibers were mechanically deformed by an applied tensile force they became highly susceptible to bacterial collagenase. This contrasts with cross-linking and tensile deformation individually protecting collagen against enzyme cleavage.

This paradoxical combination of two protective effects combining to cancel one another is surprising. Based on the collagen micro-unfolding simulations conducted using steered molecular dynamics, this effect is most likely caused by the tensile forces being transmitted through the experimentally added cross-links and causing micro-unfolding. Since thermal micro-unfolding events disrupt the collagen helix at super physiologic temperatures and thus induce susceptibility to proteolytic cleavage (Kuznetsova, McBride, and Leikin 2003), it is reasonable to expect mechanically-induced micro-unfolding to induce a similar susceptibility to proteolytic cleavage.

Although the number of tests performed in this study were relatively small, the statistical significance between the resistant and susceptible groups in the 7-day cross-linked data is clear. The plot of the EMK function vs. strain suggests a binary "Off-to-On" response for the '7-day highly cross-linked' fibers as the mechanical strain increased from 0% to 3.4% at relaxation. To statistically test for such a response, the 7-day fibers were pooled into two groups, 'high strain—easily degraded fibers' ($T_E(\epsilon)>1$) or 'low strain—highly resistant fibers' ($T_E(\epsilon)<1$). The EMK function values of the degraded and resistant groups were $T_E$=4.043±0.352 (n=3) and $T_E$=0.014±0.031 (n=5), respectively, which were statistically different (p<0.0001).

In both the 3-day and 7-day AGE cases, the response is clearly opposite from native tissue, which showed a decreasing EMK as strain increased (Wyatt, Bourne, and Torzilli 2009). The transition likely occurs when the amount of force per cross-link exceeds some minimum necessary threshold, predicted by steered molecular dynamics to be <1,000 pN for a related collagen peptide (Bourne and Torzilli 2011). (GraphPad Software Inc., La Jolla, Calif.). In addition the EMK function mean of the resistant group was not different from zero (p=0.37).

Significance and Conclusions

The studies set forth in the Examples, provide for the first time, important experimental evidence supporting the mechanical force-induced micro-unfolding predictions previously made using steered molecular dynamics models (Bourne and Torzilli 2011). More broadly these results provide new data on how the complex interplay between matrix components, matrix and tissue structure, and mechanical forces/deformations can combine to provide additional layers of biological complexity to processes such as enzyme—substrate, protein—protein, and cell—matrix interactions.

AGE cross-links results in biomechanical changes to tissues, including tissue stiffening. Beyond the structural and biomechanical effects, AGEs can influence cellular biology through the receptors for AGEs (RAGE) and appear to be a pro-inflammatory signal and/or contribute to chronic inflammation.

The work described above, and in the examples, is the first evidence that shows that combining glycation cross-linking with mechanical loading (each of which individually protect collagen from enzymatic degradation) cause accelerated enzymatic degradation. More importantly, and not obvious from previous data on AGE cross-links and enzymatic degradation, is that the combined data indicate that removing or modifying cross-links in tissues that are mechanically loaded is a method to better protect or stabilize collagenous tissues.

Thus, these scientific results lead to the conclusion that the removal of cross-links in collagenous tissues that are then loaded mechanically in vivo improves tissue survival.

Modifying, Inhibiting, Reducing and/or Eliminating AGEs or Cross-Links in Collagen in Grafts Based upon the findings set forth herein, the present invention involves a method of treating a graft, implant, scaffold or construct to inhibit, remove or modify, any or all, natural and AGE related cross-links. The treatment comprises contacting or incubating the graft, implant, scaffold or construct, with at least one AGE or collagen cross-link inhibitor, remover or modifier for a period of time and at a temperature sufficient to inhibit, remove or modify the AGE or collagen cross-link.

The treatment may also comprise rinsing the tissue at least one time, until the AGE or collagen cross-link inhibitor, remover or modifier is no longer meaningfully present in the tissue. Alternatively, the AGE or collagen cross-link inhibitor, remover or modifier could be left in the tissue and not rinsed out.

It is contemplated that this method be added as a step in the processing of grafts. For allografts or xenografts or prosthetics, this treatment step could be performed at any stage in process after tissue harvesting and before final sealing of the packaged product.

Alternatively, for allografts and xenografts, as well as for autografts, the treatment step could be performed at the hospital or other medical center, just before or during the actual implantation procedure.

The period of time for which the tissue is incubated with the inhibitor, remover or modifier of cross-links may be between 1 minute and 72 hours, depending on treatment concentration and the materials being treated, and can be determined by the skilled practitioner.

The amount and concentration of the inhibitor, remover or modifier of cross-links that is applied will vary, in part, based on the actual treatment selected. Alagebrium, a preferred agent for use, may be used at concentrations of between about 100 and 500 mM for about 1-120 minutes or between about 0.1 mM and 250 mM for about 4-16 hours.

Another preferred agent for use is C36, which may be used at a concentration of between about 1 mM and 150 mM for about 1-120 minutes or between about 0.05 mM and 250 mM for about 4-16 hours.

The agents for use in this method have reasonable activity at a range of different temperatures and the activity of the agent results in more or less time needed to achieve cross-link removal. In other words, lower activity can be compensated by increasing contact or incubation time and vice versa. However, most agents work at a temperature range of about 4° C. to 37° C.

Grafts

Tissue, or matrix into which endogenous tissue may form and grow, is grafted onto humans, animals, and plants for a variety of reasons and from a variety of sources. The results herein show that the use of AGE and cross-link inhibitors or breakers to treat grafts to remove or modify extracellular matrix AGE or cross-links are useful for preventing the failure of those grafts once they are surgically implanted and placed under mechanical forces.

Any graft, implant, scaffold or construct suitable for implantation into a mammal for the treatment, repair or replacement of defects or injury in biological tissue, whether from natural or synthetic sources, can be treated with an AGE or cross-link inhibitor and will be predicted to have improved surgical outcomes. The only pre-requisite is that there must be collagen present in at least some portion of the graft, implant, scaffold or construct, as it is the cross-links in the collagen that are to be eliminated or reduced in order to decrease enzymatic degradation and failure, and increase the positive outcome of the implantation of the graft.

Any graft from a natural source, including autologous, isogeneic, allogeneic, and xenogeneic would necessarily have collagen present.

Many grafts, implants, scaffolds, and constructs which are made of synthetic materials and considered prosthetic or artificial, have a collagen component even if a portion of the graft is made of synthetic materials, such as metal, plastic, ceramic, or polymer.

Grafts May be Classified as Follows:

Autologous: The donor tissue is taken from a different site on the same subject (also known as an autograft).

Isogeneic: The donor and recipient are genetically identical (e.g., monozygotic twins; animals of a single inbred strain; isograft or syngraft).

Allogeneic: The donor and recipient are of the same species (human→human, dog→dog; allograft).

Xenogeneic: The donor and recipient are of different species (e.g., bovine cartilage; xenograft or heterograft).

Prosthetic: Lost tissue is replaced with synthetic nondegradable materials such as metal, plastic, or ceramic (prosthetic implants), and/or biodegradable materials such as polylactic acid (PLA), polyglycolic acid (PGA) and poly(lactic-co-glycolic acid) (PLGA).

Semi-synthetic/Hybrid biologic-synthetic: a graft fashioned of synthetic and biologic biodegradable and/or nondegradable materials.

In medical and veterinary contexts, many tissues can be grafted: skin, bone, nerves, tendons, neurons, blood vessels, fat, and cornea are tissues commonly grafted today.

Specific Types Include:

Tendon or ligament grafting. For example, in anterior cruciate ligament (ACL) reconstruction procedures, the patellar tendon, anterior tibialis tendon, Achilles tendon, or hamstring tendon (most commonly made with the semitendinosus tendon either alone, or accompanied by the gracilis tendon) may be taken from the patient, or recovered from a cadaver, and used in reconstruction. Another example is ulnar collateral ligament (UCL) reconstruction.

More generally in the field of orthopedics, commonly used allografts in orthopedic procedures include:

Bone:

Demineralized bone products (osteoinductive);

Cortical/cancellous—powder, chips, wedges, dowels, crest, pegs, and screws;

Structural—cortical segments, shafts, long bones, pelvis, acetabulum;

Osteochondral long bone (cryoprotected cartilage); and

Ribs, mandible, calvarium, ear ossicles.

Soft Tissue:

Patellar ligament and Achilles tendon (bone block), other assorted tendons;

Fascia lata, rotator cuff;

Cartilage and osteochondral segments (fresh and cryoprotected);

Meniscus (fresh and cryoprotected);

Costal cartilage;

Skin grafting is often used to treat skin loss due to a wound, burn, infection, or surgery. In the case of damaged skin, it is removed, and new skin is grafted in its place. Skin grafting can reduce the course of treatment and hospitalization needed, and can also improve function and appearance.

Bone grafting is used in dental orthopedic implants, as well as other instances. The bone or other grafted substance, may be autologous, typically harvested from the iliac crest of the pelvis, or banked bone. One example of bone graft material is Sunmax Collagen Bone Graft Matrix, which is a mixture consisting of bioresorbable purified fibrillar collagen and hydroxyapatite/β-tricalcium phosphate (HAp/β-TCP) ceramic. The highly purified collagen component is porcine dermal type I collagen. Another example is Mucograft® Collagen Matrix made by Osteohealth, which is indicated for covering of implants placed in immediate or delayed extraction sockets, localized gingival augmentation to increase keratinized tissue (KT) around teeth and implants, alveolar ridge reconstruction for prosthetic treatment and guided tissue regeneration procedures in recession defects for root coverage.

Vascular grafting is the use of transplanted or prosthetic blood vessels, or matrix into which vessel tissue may grow, in surgical procedures. One example of a vascular graft is the Artegraft, which is a bovine carotid artery graft that consists of a biological fibrous matrix processed to enhance long-term patency and provide a tightly woven, cross-linked conduit that is flexible and compliant.

Other forms of grafting may be done, which may also be considered the use of extracellular matrix, or collagen-based matrices, or tissue as a medical device or a component of a medical device. For instance, collagen-based matrix can be used in soft tissue reconstruction procedures. One example is the XENMATRIX™ Surgical Graft, which is non-cross-linked, regenerative porcine collagen matrix for hernia and abdominal wall repair. Another example is ALLOMAX™ Surgical Graft for Hernia and Abdominal Wall Repair, which is sterile, non-cross-linked, regenerative human collagen matrix for soft tissue repair, including hernia and abdominal wall reconstruction.

Another example is an absorbable collagen hemostat, such as that under development by Sunmax, in the form of sheets or powder. The collagen may be highly purified from tissue, for example, from porcine skin, and may be manufactured into a sheet or flour form. It could be indicated as an adjunct to hemostasis to control bleeding by ligature or when conventional procedures are ineffective or impractical.

Similarly, tissue or matrix can be used to promote wound healing. For example the OASIS® Wound Matrix, which is an extracellular matrix derived from porcine small intestinal submucosa, is indicated for the management of diabetic, pressure, venous, and chronic vascular ulcers, trauma (including burns), drainage, surgical, and partial- and full-thickness wounds.

Another such product is collagen-based dermal implants, which are injectable devices comprising collagen, for example porcine dermal collagen, which after preparation may be packaged with a sterile needle. Such dermal implants may be used for cosmetic surgery.

Another example is the use of tissue or matrix as a sling, for example as a pubovaginal sling in female patients with stress urinary incontinence (SUI).

A further example of grafts or implants are those made, in part, of synthetic materials for use in treating, replacing and/or repairing biological tissue, but which also comprise a portion that contains collagen. In these grafts, collagen biomaterial has been added to the synthetic material in order to facilitate the graft or implant integration into the biological tissue. Examples of this type of graft or implant include hybrid implantable collagen-polymer hydrogels and collagen-synthetic materials such as those described U.S. Pat. No. 5,475,052.

Other examples of synthetic implants coated with collagen would include devices that implanted into a subject to monitor and/or facilitate organ or tissue function, such as glucose monitors, defibrillators, and pace makers. These monitors would be coated with collagen again to facilitate the implant's integration into the biological tissue in which it is implanted.

Tissue Processing of Allografts from Donors and of Xenografts

Similar to organ donation, most allograft tissue is recovered surgically after someone dies. The gift of tissue donation is strictly voluntary and must be generously given by the donor prior to death or the donor's family.

After consent for donation is obtained, potential donors are screened for risk factors associated with infectious diseases and medical conditions that would rule out donation. The donors are physically examined to seek evidence of active infection (viral, bacterial, or fungal); sexually transmitted diseases, such as genital ulcerative disease, herpes simplex, syphilis and chancroid; needle tracks (nonmedical); recent tattoos and piercings (within past 12 months); lymph node enlargement; jaundice, icterus, hepatomegaly; blue/purple (gray/black) spots consistent with Kaposi's sarcoma; evidence of anal intercourse (perianal lesions, insertion trauma); unexplained oral thrush; trauma or infection to recovery sites; and clinically significant skin lesions (rash, scabs). Additionally, tests are done for infectious disease, including: HIV 1/HIV 2 Antibody/HIV-1 NAT; HB Core Antibody (total, IgM and IgG); HBsAg; HCV Antibody/HCV NAT; Syphilis test (*T. pallidum*); and HTLV-I/II Antibody.

Donated tissues are recovered by a tissue recovery agency using aseptic surgical techniques for up to 24 hours after a person's heart stops beating.

The tissue is then sent to a tissue processing facility, which prepares the tissue for transplantation. Laboratory testing to screen for infectious diseases is performed on each donor's blood and a licensed physician makes a final determination of donor suitability.

Tissues are then processed in a strictly controlled clean environment, minimizing the risk of airborne and other contaminants Tissues are cleaned and otherwise processed, sectioned and formed into precision-shaped implants, demineralized bone matrix (DBM) implants or conventional allografts. Tissue banks also develop proprietary tissue sterilization technologies.

The cleaning and processing of tissue may take many forms. The processing may be temperature-based, mechanical and/or chemical. The mechanical component may involve application of pressure or stirring. The chemical component may involve use of detergents, sterilants, rinses, oxidative agents, acidic agents, alkaline agents, alcohol-based agents, dehydrating agents, and/or humectants. If tissue is frozen, cryopreservatives such as DMSO (dimethyl sulfoxide), ethylene glycol, glycerol, 2-Methyl-2,4-pentanediol (MPD), propylene glycol, or sucrose may be used. Gamma irradiation may be used to ensure the sterility of the final packaged product.

The goals of the processing may include break down cell walls, removing or retaining cells, inactivating and/or removing bacteria and/or other pathogens, and/or preserving the structure of proteins and/or other biomolecules, such as collagen.

The finished implants are distributed to healthcare facilities for surgeons to implant.

Under federal law, all establishments dealing with recovery, processing and distribution of human donated tissue operating in the United States must be registered with the Food and Drug Administration (FDA) and must adhere to applicable FDA regulations, including the Current Good Tissue Practices (cGTPs), which means they must: possess a Quality Control/Quality Assurance Program; eliminate or reduce blood, debris and cells from allografts to reduce disease transmission potential; validate bacteriologic and virucidal washes and/or treatments; evaluate bacteriologic bioburden (we-processing and in-processing cultures to evaluate contamination); possibly use gamma radiation 10-18 kilogray (10 kilogray~1 Mrad) or more (non-terminal or terminal sterilization); conduct final product testing for bacteriologic contamination (swabs, immersion, or destructive testing); discard tissue or donor lot based on certain types of early bacteriologic contamination (e.g., *Streptococcus* Group A, *Clostridium*); and conduct final review by tissue bank medical director of screening/testing prior to release of tissue for transplantation. Periodic inspections by the FDA are part of the registration process. Some tissue banks have voluntarily submitted to an accreditation process through the American Association of Tissue Banks, which also includes periodic inspections. Tissue banks must also comply with the applicable laws of the states in which they operate.

Another step that is sometimes conducted while processing biological tissues is the intentional chemical cross-linking of extra cellular matrix components such as collagen. Agents used in this process include but are not limited to: glutaraldehyde; diphenylphosphorylazide (DPPA); ethyldimethylaminopropyl carbodiimide (EDAC); acyl azides; glycidyl ethers; diisocyanates; hexamethylenediisocyanate; bis-epoxide; carbodiimide; dimethylsuberimidate; and nordihydroguaiaretic acid. Enzymes may be used to cross-link, as may light, such as ultraviolet light. Heat may be used. Methods combining any of heat, light, chemicals, and/or enzymes may be used.

Currently, even though many tissues are taken from cadavers of people who die from old age, no process is conducted to attempt to "rejuvenate" tissues prior to implanting them in patients who may be much younger than the donor. Likewise, xenografts are not rejuvenated.

Thus, based upon the work set forth herein, further procedures to remove AGE and/or collagen cross-links should be performed.

Tissue Processing of Autografts

When tissue is to be taken from the patient into whom that tissue will be implanted elsewhere, the general procedural steps include:
harvesting the tissue;
debriding/trimming edges and surfaces;
washing and rinsing with sterile saline or other solution;
sizing the autograft;
washing and rinsing with sterile saline or other solution;
placing sutures or other fixation devices;
mark the autograft to ensure proper orientation;
washing and rinsing with sterile saline or other solution; and
placing and fixing the autograft Generally there is no step in the autograft procedure related to rejuvenating the tissue between the time it is removed, and the time it is implanted.

One example of age-related effects on tissue, is the prevalence of advanced glycation endproducts (AGE), which increases dramatically in tissue with age and which the work herein has shown affects the tissue's mechanical and biochemical properties.

AGE Inhibitors or Breakers

Compounds that inhibit AGE formation or that break AGE crosslinks, are known in the art.

Preferred AGE inhibitors or breakers include, but are not limited to:
Alagebrium [3-phenacyl-4,5-dimethylthiazolium chloride, also known as 4,5-dimethyl-3-(2-oxo-2-phenylethyl)-thiazolium chloride, formerly known as ALT-711];
ALT-462;
ALT-486;
ALT-946;
N-phenacylthiazolium bromide (PTB);
4,5-dimethyl-3-phenylacylthiazolium chloride (DPTC)
TRC4186 as described in Joshi et al. 2009, which is incorporated herein in its entirety by reference;
TRC4149, as described in Pathak et al. 2008, which is incorporated herein in its entirety by reference;
C36 as described in Cheng et al. 2007 which is incorporated herein in its entirety by reference; and
C16 as described in Cheng et al. 2005 which is incorporated herein in its entirety by reference.

Additionally the following compounds, described in Rahbar and Figarola 2003 which is incorporated herein in its entirety by reference, are preferred AGE inhibitors:
LR-20 [which is L-bis-4[-(4-chlorobenzamidophenoxy-isobutyryl)cystine]];
LR-23 [which is 4-(3,5-dichlorophenylureido)-phenoxy-isobutyryl-1-amidocyclohexane-1-carboxylic acid];
LR-99 [which is 4-[(3,5-dichlorophenylureidophenoxy-isobutyryl]-4-aminobenzoic acid)];
LR-102 [which is 1,4-benzene-bis[4-methyleneaminophe-noxyisobutyric acid]];
SMR-5 [which is 5-aminosalicylic acid or 5-ASA];
SMR-12 [which is dimethylbiguanide or metformin]; and
LR-90 [which is methylene bis[4,4'-(2-chlorophenylure-idophenoxyisobutyric acid)].

Additional AGE treatments, include, but are not limited to:
benfotiamine;
pyridoxamine;
pimagedine (aminoguanidine HCl);
alpha-lipoic acid;
taurine;
aspirin;
carnosine;
desferrioxamine;
penicillamine;
pioglitazone;
pentoxifylline;
metformin;
2-isopropylidenehydrazono-4-oxo-thiazolidin-5-ylacetanil-ide (OPB-9195);
2,3-diaminopropionic acid (Dap) and N-terminal Dap peptides as described in Sasaki et al. 2009, incorporated herein in its entirety by reference;

amadorins;
pyruvate;
nicarnitine; and
losartan.

Additionally the following compounds, described in Rahbar and Figarola 2003, which is incorporated herein in its entirety by reference, are additional AGE inhibitors:

LR-9 [which is 4-(2-naphtylcarboxamido)phenoxyisobutyric acid];
LR-33 [which is 4-(2-chloro-4-nitrophenylureido)phenoxyisobutyric acid];
LR-41 [which is 4-(3-chloro-4-fluorophenylureido)phenoxyisobutyric acid];
LR-59 [which is 4-[(3,4-dicholorophenylmethyl) 2-chlorophenylureido]phenoxyisobutyric acid];
LR-62 [which is 4-(2,4-dichlorophenacylamino)phenoxyisobutyric acid]; and
LR-74 [which is 2-(8-quinolinoxy)propionic acid].

Kits

Also provided for in the current invention are kits comprising an effective dose or doses of at least one AGE or collagen cross-link inhibitor, remover or modifier agent and instructions for use. The kit may also comprising one or more rinsing solutions, which would include but is not limited to, saline, and/or a solvent that is not damaging to tissue but that effectively removes the AGE inhibitor as is known in the art. The kit may also comprise one or more devices that serve to contain the graft, implant, scaffold or construct and the AGE inhibitor, modifier or removal agent. The device can provide some form of mechanical perturbation, e.g., shaking or agitating. The device can also provide a means to maintain the tissue in a specific shape.

EXAMPLES

The present invention may be better understood by reference to the following non-limiting examples, which are presented in order to more fully illustrate the preferred embodiments of the invention. They should in no way be construed to limit the broad scope of the invention.

Example 1

Experimental Procedures

Chemicals

Dulbecco's PBS with calcium ($CaCl_2$, 0.133 mg/ml) and magnesium ($MgCl_2$, 0.1 mg/ml) and D-Ribose (99% pure) was purchased from Sigma-Aldrich (St. Louis, Mo.), 10× concentrated PBS from Invitrogen (Carlsbad, Calif.), and thymol crystals were from Fisher Chemical Company (Fair Lawn, N.J.). Type II bacterial collagenase (CLS-2, purified from *Clostridium histolyticum* with reported activity of 245 units/mg dry weight) was purchased from Worthington Biochemical Company (Lakewood, N.J.).

Rat Tail Tendon Collection and Glycation

Rat tails were collected from 6 month old Lewis rats euthanized for unrelated studies in accordance with institutional animal care and use committee approved procedures. Tails were sectioned between the proximal caudal vertebrae and freeze-thawed twice to decellularize the tissue, then stored at −80° C. until tendons were harvested. To collect tendon fibers the tails were first thawed at room temperature for approximately 60 minutes and then the distal tip of the tail was removed, leaving an approximately 100 mm length tail specimen. Tendon microfibers (i.e., fascicles of about 300 μm diameter) were teased out from the distal end of the tail, immediately soaked in 15 ml of PBS and then separated into treatment groups. Tendons were either immediately stored in PBS at 4° C. (0 days, no ribose exposure) or were glycated by ribose exposure.

Glycated specimens were prepared as previously described (Bai et al. 1992; Tanaka et al. 1988). Tendons were incubated at 0.2 M ribose solutions at 37° C. with a crystal of thymol to prevent bacterial growth for 3 or 7 days of exposure. The specimens incubated for 7 days had the ribose solution exchanged with fresh 0.2 M ribose solution at the 3-day point. At the end of the ribose incubation, the fibers were rinsed for 5 minutes with PBS to remove free ribose, and then stored in fresh PBS at 4° C. until used for mechanical testing.

Relative Fluorescence Measurements

Ribose incorporation into fibers over time was assessed by fluorescence of solubilized fibers following 0 to 10 days of incubation (Verzijl et al. 2002). Fibers were incubated in 0.2 M ribose solution (solution was exchanged with fresh ribose solution at day 3) and sample fibers were removed daily, rinsed in PBS, and then stored at 4° C. until the end of the time course. Fibers were weighed, then dissolved at 60° C. in a 1:20 dilution of papain (Carica Papaya, Roche Diagnostics, Indianapolis, Ind.) in buffer per the commercial protocol at a concentration of 1 mg tendon per 50 uL of papain solution. Relative fluorescence was measured at about 460 nm using a spectrophotometer (340 ATTC, Tecan US, Chapel Hill, N.C.) as reported by Verzijl et al. 2002. Maximum fluorescence was estimated from measurements of fibers incubated in ribose for 5 weeks.

Unloaded Fiber Enzyme Susceptibility Test

In order to test for differential collagenase digestion susceptibility, fibers from the two treatment groups were incubated in a 1% by weight bacterial collagenase solution dissolved in Dulbecco's phosphate buffered saline (PBS) with calcium and magnesium at room temperature (about 22° C.). Enzymatic digestion of the fibers was tracked by observing for visible fiber dissolution with digital images captured periodically. A needle of known diameter was included in each image and used as a reference to calculate the diameter of the fibers using ImageJ (ImageJ, U.S. National Institutes of Health, Bethesda, Md.). To control for variations in enzyme activity, fibers of comparable size from the same animal were incubated side-by-side in a single shared enzyme bath. This was repeated three times with fibers from three different tails.

Collagen Enzyme Mechano-Kinetic Automated Test System

This study utilized the Collagen Enzyme Mechano-Kinetic Automated Test System (CEMKATS) as described by Wyatt, Bourne and Torzilli, with only minor changes to the previously published testing and data analysis protocol (Wyatt, Bourne, and Torzilli 2009). A schematic of the test system is shown as FIG. 1.

To briefly describe the CEMKATS setup, a relaxation test was performed using two axially opposed computer-controlled stepper motors to apply a tensile load to a fiber at a maximum velocity of 1 mm/s. When a pre-calculated clamp-to-clamp strain was reached, the motors were stopped to maintain the strain for the remainder of the experiment. The tensile force in the fiber was measured with a 250 gm load cell for the entirety of the test. An inverted microscope magnified two inked marks on the fiber, which were recorded using a digital camera via a second computer for use in calculating local strain measurements. The real-time in-situ fiber strain is determined from the distance separation of the two marks on the fiber, shown as Local Strain Measurements in the figure.

Following a test the local strains in the specimen at peak load and relaxation were calculated by using NIH ImageJ software to measure the distance between the inked marks on the fiber.

Although the protocol was nearly identical to that reported by Wyatt et al. 2009, several small modifications were made in the test setup. Marks on the tendon were made using an industrial grade permanent marker (Sharpie™, Newell Rubbermaid, Oak Brook, Ill.) or inkjet printer ink. The channel was etched in a block of plastic with dimensions of 26 mm wide, 1.5 mm across, and 1 mm deep. The smaller channel and smaller gaps (<1 mm) between the channel and the grips allowed the use of a slow continuous PBS drip at about 2-3 drops/minute instead of the higher about 1 drop/second rate used in the original study (Wyatt, Bourne, and Torzilli 2009).

One major revision to the previously published protocol was that the fibers in the present study were now allowed to completely relax to a constant equilibrium load before adding the enzyme. This simplified data analysis as it allowed the direct measure of the decrease in load as a result of enzyme cleavage of the fiber without having to deconvolute the enzyme cleavage response from the stress-relaxation response.

As described earlier by Wyatt et al., the enzyme cleavage was described by an EMK relaxation function, $T_E(\epsilon)$, which is a function of applied strain, $\epsilon$ and time t. $T_E$ was directly assessed for each applied strain by measuring the change in stress ($\sigma$, with the enzyme cleavage phase indicated with subscript e) as a function of time and normalized to the equilibrium stress (relaxation indicated with subscript r) of that fiber; the equation for $T_E$ is shown symbolically below as Equation 1 (Wyatt, Bourne, and Torzilli 2009).

$$T_E(\epsilon)=[d\sigma_e(t)/dt]/\sigma_r \quad \text{(Equation 1)}$$

Example 2

Results of the Unloaded Fiber Enzyme Susceptibility Test

Tendon microfibers were tested for susceptibility to enzymatic degradation in an unloaded state by observing fiber digestion to dissolution over an approximate 24 hour period as described in Example 1. Comparable diameter tendon microfibers were obtained from the same animal tail and treated with 0.2 M ribose for 0, 3 or 7 days and then incubated unloaded in bacterial collagenase. Representative images at the air—collagenase interface of the fibers were digitally recorded at the 0 hours (start) and after 5 and 25 hours of collagenase exposure.

In all 3 tests, the 0-day non-glycated fiber degraded and dissolved fastest, followed by the 3-day glycated fiber. The 7-day glycated fiber showed no visible degradation after prolonged enzyme exposure.

Representative results from one experiment are shown in FIG. 2. In these results, the 0-day non-glycated (native, no cross-linking) fiber dissolved after approximately 5 hours of exposure, while the 3-day glycated fiber completely degraded between 5 and 24 hours of enzyme exposure. At the conclusion of the test, the 7-day glycated fiber was intact with no visible degradation even after more than 25 hours of enzyme exposure, and had persisted approximately five times longer in the enzyme solution than was needed to completely dissolve a 0-day non-glycated fiber.

Example 3

Results of Tensile Strain at Equilibrium

Previous mechanical relaxation tests using native non-glycated rat tail tendon microfibers have shown an unusual increase in the tensile strain between the end of loading (peak strain) and stress relaxation (equilibrium strain) of the tissue. Therefore, the mechanical relaxation strain response between native and cross-linked tissue was compared.

The peak and equilibrium strains from the mechanical relaxation tests for the glycation cross-linked fibers as described in Examples 1 and 2 (triangles) were compared to historical data for native fibers (squares) from our previous study (Wyatt Bourne and Torzilli 2009). The peak and equilibrium strains were plotted and the relationship between them was fit with a linear regression model (regression+95% confidence intervals as solid and dotted lines respectively) using SigmaPlot 10 software (Systat Software, Inc., Chicago, Ill.).

Analysis of the peak and equilibrium strains for the 3-day glycated fibers (n=4) and 7-day fibers glycated fibers (n=5) from Example 2 found no statistical difference in the strains (peak-equilibrium, p=0.15) between the two days, so the data was combined (n=9) for the remainder of the peak and equilibrium strain data analysis between the native and cross-linked fibers.

A scatter plot of the peak and equilibrium strains for the native and cross-linked fibers is shown in FIG. 3. A regression analysis was performed for the native and cross-linked fibers using a linear (straight-line) fit to the equilibrium vs peak strain data (SigmaPlot 10, Systat Software, Inc., Chicago, Ill.). The slope of the mean regression line for the cross-linked fibers was 1.21±0.64 (mean standard deviation, r=0.907, n=9) which was not statistically different from unity (i.e., peak=equilibrium, p<0.351), while the slope for the native fibers 1.45±0.88 (r=0.865, n=23) was different from unity (p=0.022). However the two slopes could not be statistically distinguished from each other (p=0.461).

Compared to their respective peak strains, the native fibers' equilibrium strain was 45% greater after relaxation (n=23) while the glycation cross-linked fibers' equilibrium strain was only 25% greater (n=9).

Taken together these data suggest that the cross-linking causes the tendon microfiber mechanical relaxation response to behave closer to a viscoelastic material in which the applied peak strain does not change during stress relaxation ($\epsilon_r/\epsilon_p$ ratio of unity). These results are in agreement with Purslow et al., where it was also found strain increases during stress relaxation which appeared to be due, at least in part, to structural rearrangements that were restricted by the collagen-collagen intermolecular cross-links (Purslow, Wess, and Hukins 1998).

Example 4

Results of CEMKATS Enzymatic Degradation

Glycation cross-linked microfibers treated for 3 days with ribose ("3-day moderately cross-linked") and 7 days ("7-day highly cross-linked") with ribose as described in Example 1 were tested for enzyme cleavage susceptibility during different amounts of applied uniaxial tensile deformation (1.3% to 3.4% equilibrium strain) using CEMKATS as described in Example 1.

In contrast with unloaded fibers' resistance to enzyme degradation, the cross-linked tendon microfibers under increasing mechanical strain appeared to become highly susceptible to enzymatic degradation. There was increasing cleavage for the 3-day moderately cross-linked and 7-day highly cross-linked fibers with increasing mechanical strain, as indicated by higher EMK Function ($T_E$) values with increasing strain (shown as a scatter plot in FIG. 4A).

Figure 4:
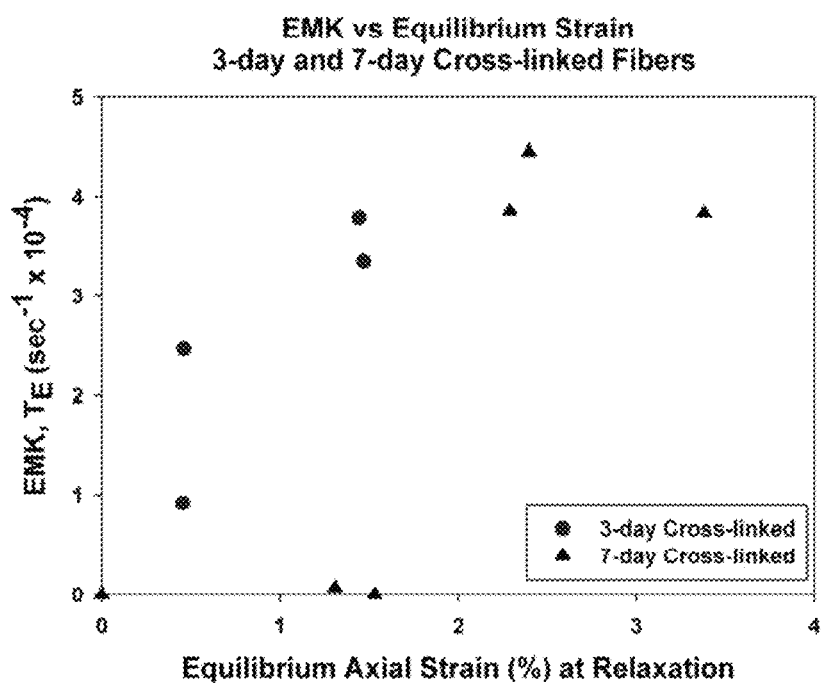
FIG. 4 are graphs of enzyme mechano-kinetic, (EMK) function versus equilibrium strain as shown by CEMKATS.
Figure 4:
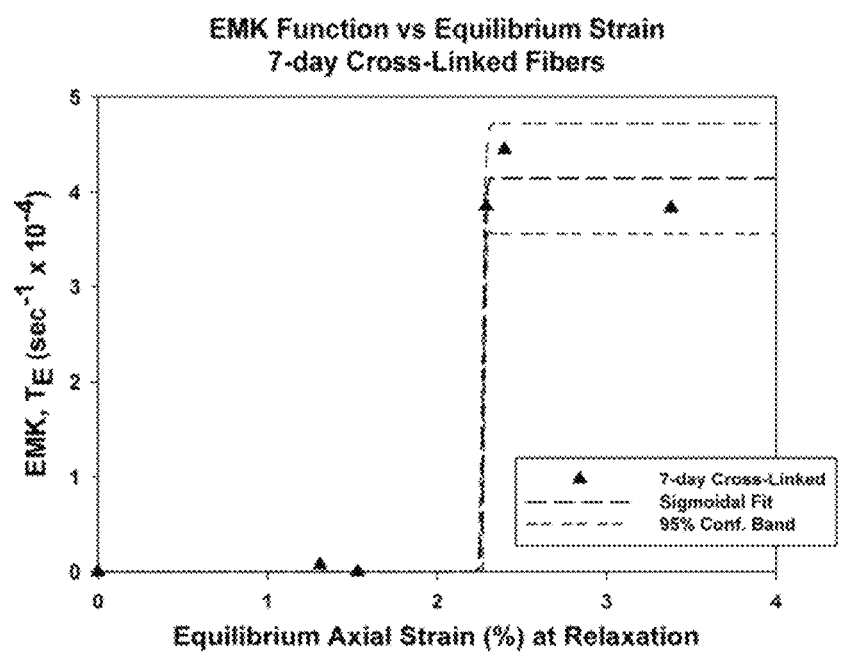

The 7-day highly cross-linked fibers data was well-described by a 3-parameter sigmoidal function, suggesting an "off-to-on" transition as applied strain increased as shown in FIG. 4B.

The plot of the EMK function vs. strain suggests a binary "Off-to-On" response for the '7-day highly cross-linked' fibers as the mechanical strain increased from 0% to 3.4% at relaxation. To statistically test for such a response, the 7-day fibers were pooled into two groups, 'high strain—easily degraded fibers' ($T_E(\epsilon)>1$) or 'low strain—highly resistant fibers' ($T_E(\epsilon)<1$). Data from the unloaded tests (n=3, Results 2.1) was included as $T_E(0)=0$ (0% strain, no cleavage) in the low-strain group for statistical analysis. The EMK function values of the degraded and resistant groups were $T_E=4.043\pm0.352$ (n=3) and $T_E=0.014\pm0.031$ (n=5), respectively, which were statistically different (p<0.0001) (GraphPad Software Inc., La Jolla, Calif.). In addition the EMK function mean of the resistant group was not different from zero (p=0.37).

Example 5

Results of Fluorescence Testing

Figure 5:
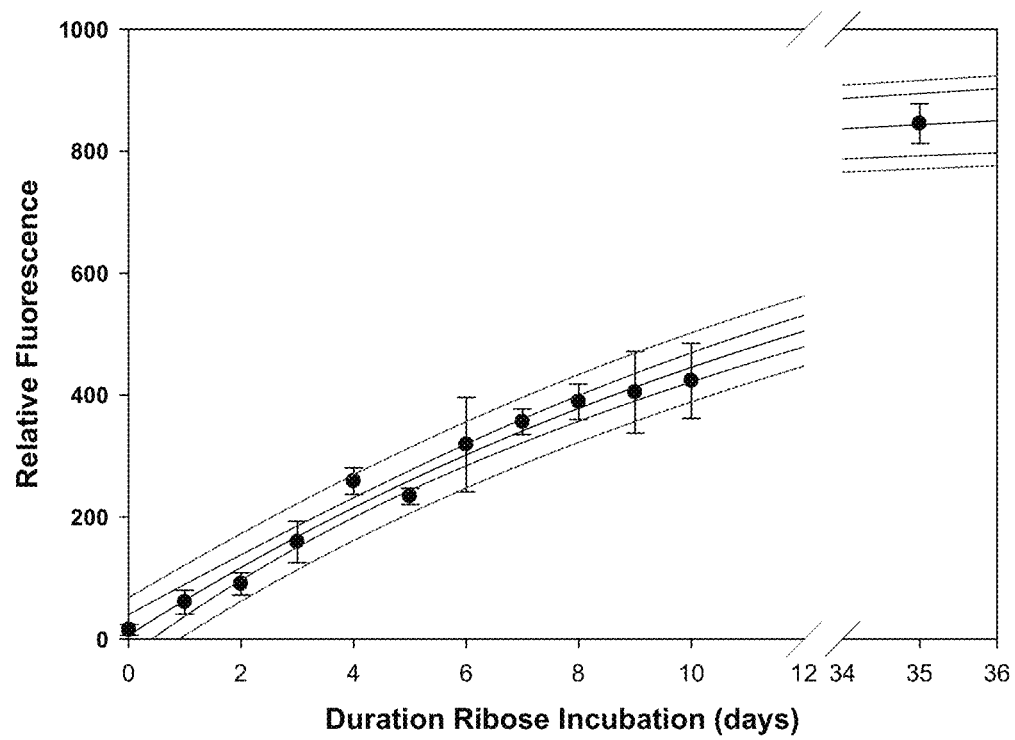
FIG. 5 is a graph of relative fluorescence versus duration of ribose incubation in days.

Relative fluorescence, as described in Example 1, showed that 7 days of ribose exposure significantly increased the relative fluorescence of the solubilized rat tail tendon, as shown in FIG. 5, due to the accumulation of sugar based cross-links in the tendon.

Example 6

In Vitro Treatment of Grafts

Materials and Methods 7-day glycated (cross-linked) tendon fibers are immersed for 12 hours in a solution of 15 mM Alagebrium dissolved in PBS at a temperature ranging from about 4° C. to 37° C. The fibers are removed from the solution, rinsed in PBS, and then soaked in fresh PBS for 15 minutes. After this soak, the fibers are removed from the PBS bath, rinsed with fresh PBS. The visible PBS is blotted off and the fibers are interfaced with the CEMKATS system. Mechanical strain is applied as described in Example 1. The fiber reaches a peak stress during loading and subsequently relaxes to an equilibrium stress. Once the specimen reaches equilibrium, collagenase would be added. The resulting change in load would be observed and recorded (which would be converted post-hoc to stress).

Results

In tests at low strain (less than about 1.25%), the cross-linked fibers (control specimens) are more resistant to degradation than the cross-link broken (Alagebrium-treated specimens) fibers. This is observable by the EMK function values (described above), which are lower for controls than Alagebrium-treated specimens. In contrast, tests with a higher strain (above about 3%) show control specimens degrading faster than the Alagebrium-treated specimens, quantified by the EMK function values which have a higher value for the control specimens than the Alagebrium-treated specimens.

Example 7

Treatment of Musculoskeletal Grafts at a Tissue Bank

Materials and Methods

For an ACL reconstruction, a bone-patellar tendon-bone graft (other eligible grafts include hamstring tendon) is harvested from a cadaveric donor per standard collection procedure. Before freezing, the graft tissue is immersed in a sterile filtered isotonic buffered saline solution containing Alagebrium at a concentration of 0.1 mM for 8 hours at a temperature of ranging from about 4° C. to 37° C. Following incubation with the cross-link breaking reagent, the specimen is rinsed with sterile isotonic buffered saline and then is immersed in a rinsing fluid, such as sterile isotonic buffered saline, with a volume of at least 10 times greater than the estimated volume of the specimen. The specimen remains immersed in the rinse fluid for 30 minutes. The rinsing and immersion step is repeated twice more with fresh rinse solution each time. The tissue specimen is then removed from the fluid, excess liquid is allowed to drain, any visible fluid is gently blotted off with sterile gauze, and is then frozen as per standard procedure.

Results

This procedure results in an isolated tissue specimen that has significantly decreased amounts of AGE cross-links, which is shown by a reduction in the AGE associated absorption peak on an Fourier Transform Infrared (FTIR) spectrum. This treated specimen is less stiff after treatment and when transplanted as part of an ACL reconstruction procedure results in improved surgical outcome.

In a randomized control trial comparing Alagebrium-treated grafts with untreated grafts for an ACL reconstruction, treatment results in a lower relative risk of a negative outcomes, such as a Lachman test grade higher than 0 for joint laxity, a positive pivot-shift test, or anterior tibial translation of greater than 3 mm on an anterior force test ("Drawer" test) for the Alagebrium-treatment group at 6 and 12 months post-surgery.

Example 8

Treatment of Musculoskeletal Grafts in the Operating Room

Materials and Methods

For an ACL reconstruction, a bone-patellar tendon-bone graft (other eligible grafts include hamstring tendon) is harvested from the patient as per standard collecting procedure. Before use, the graft tissue is wrapped in sterile gauze and is soaked in a sterile filtered isotonic buffered saline solution containing Alagebrium at a concentration of 100 mM for 15 minutes at a temperature ranging from about 4° C. to 37° C. Following incubation with the cross-link breaking reagent, the specimen is unwrapped, rinsed with sterile istonic buffered saline and then is wrapped again with sterile gauze and immersed in a rinsing fluid, such as sterile isotonic buffered saline, with a volume of at least 10 times greater than the estimated volume of the specimen. The specimen remains immersed in the rinse fluid for 15 minutes. The tissue specimen is then removed from the fluid, unwrapped, excess liquid is allowed to drain, any visible fluid is gently blotted off with sterile gauze, and then the graft is utilized as per standard procedure.

Results

This procedure creates an autologous isolated tissue specimen that has significantly decreased amounts of AGE cross-links, as measured by a reduction in the AGE associated absorption peak on FTIR spectrum, which when transplanted as part of an ACL reconstruction procedure results in an improved surgical outcome.

In a randomized control trial comparing Alagebrium-treated grafts with placebo-treated grafts for an ACL reconstruction, treatment results in a lower relative risk of a negative outcomes, such as a Lachman test grade higher than 0 for joint laxity, a positive pivot-shift test, or anterior tibial translation of greater than 3 mm on an anterior force test ("Drawer" test) for the Alagebrium treatment group at 6 and 12 months post-surgery.

Example 9

Treatment of Vascular Grafts in the Operating Room

Materials and Methods

Graft tissues used for autografts in vascular surgery requiring an autologous graft include saphenous vein for peripheral vascular surgery to treat peripheral arterial disease (also known as peripheral artery occlusive disease) and internal thoracic artery (also known as internal mammary artery) for surgeries including coronary artery bypass. The graft is harvested from the patient as per standard collecting procedure. Before implantation, the graft tissue is immersed in a sterile filtered isotonic buffered saline solution containing C36 at a concentration of 100 mM for 15 minutes at a temperature ranging from about 4° C. to 37° C. Following incubation with the cross-link breaking reagent, the specimen is rinsed with sterile isotonic buffered saline and then is immersed in a rinsing fluid, such as sterile isotonic buffered saline, with a volume of at least 10 times greater than the volume of the specimen. The specimen remains immersed in the rinse fluid for 15 minutes. This rinse and immersion step is repeated once more. The tissue specimen is then removed from the rinse fluid, excess liquid is allowed to drain off, any visible fluid is gently blotted off with sterile gauze, and the tissue is utilized as per standard procedure.

Results

This procedure creates an autologous isolated tissue specimen that has significantly decreased amounts of AGE cross-links, the reduction of which can be measured directly by FTIR spectroscopy demonstrated by the reduction of the AGE associated absorption peak.

When transplanted as part of a randomized control trial of C36-treated versus placebo-treated grafts for vascular surgery procedure, C36 treatment results in a lower hazard rate for the treatment group, a lower relative risk of graft failure, and an improved patency rate at 10 years of follow up as compared to the reported 50% patency rate at 10 years for the current surgical procedure (Motwani and Topol 1998).

REFERENCES

Aronson, D. "Cross-Linking of Glycated Collagen in the Pathogenesis of Arterial and Myocardial Stiffening of Aging and Diabetes." [In Eng]. *J Hypertens* 21:1 (2003): 3-12.

Bai, P., K. Phua, T. Hardt, M. Cernadas, and B. Brodsky. "Glycation Alters Collagen Fibril Organization." [In Eng]. *Connect Tissue Res* 28:1-2 (1992): 1-12.

Bailey, A. J., R. G. Paul, and L. Knott. "Mechanisms of Maturation and Ageing of Collagen." [In Eng]. *Mech Ageing Dev* 106: 1-2 (1998): 1-56.

Bank, R. A., J. M. TeKoppele, G. Oostingh, B. L. Hazleman, and G. P. Riley. "Lysylhydroxylation and Non-Reducible Crosslinking of Human Supraspinatus Tendon Collagen: Changes with Age and in Chronic Rotator Cuff Tendinitis." [In Eng]. *Ann Rheum Dis* 58:1 (999): 35-41.

Bourne, J. W., and P. A. Torzilli. "Molecular Simulations Predict Novel Collagen Conformations During Cross-Link Loading." [In Eng]. *Matrix Biol* 30:5-6 (2011): 356-60.

Buehler, M. J. "Atomistic and Continuum Modeling of Mechanical Properties of Collagen: Elasticity, Fracture, and Self-Assembly." [In Eng]. *Journal of Materials Research* 21:8 (2006): 1947-61.

Camp, R. J., M. Liles, J. Beale, N. Saeidi, B. P. Flynn, E. Moore, S. K. Murthy, and J. W. Ruberti. "Molecular Mechanochemistry: Low Force Switch Slows Enzymatic Cleavage of Human Type I Collagen Monomer." [In Eng]. *J Am Chem Soc* 133:11 (2011); 4073-78.

Chen, A. C., M. M. Temple, D. M. Ng, N. Verzijl, J. DeGroot, J. M. TeKoppele, and R. L. Sah. "Induction of Advanced Glycation End Products and Alterations of the Tensile Properties of Articular Cartilage." [In Eng]. *Arthritis Rheum* 46; 12 (2002): 3212-7.

Cheng, G., L. L. Wang, L. Long, H. Y. Liu, H. Cui, W. S. Qu, and S. Li. "Beneficial Effects of C36, a Novel Breaker of Advanced Glycation Endproducts Cross-Links, on the Cardiovascular System of Diabetic Rats." [In Eng]. *Br J Pharmacol* 152:8 (2007): 1196-206.

Cheng, G., L. L. Wang, W. S. Qu, L. Long, H. Cui, H. Y. Liu, Y. L. Cao, and S. Li. "C16, a Novel Advanced Glycation Endproduct Breaker, Restores Cardiovascular Dysfunction in Experimental Diabetic Rats." [In Eng]. *Acta Pharmacol Sin* 26:12 (2005): 1460-6.

Choudhary, M. I., G. Abbas, S. Ali, S. Shuja, N. Khalid, K. M. Khan, Rahman Atta ur, and F. Z. Basha. "Substituted Benzenediol Schiff Bases as Promising New Anti-Glycation Agents." [In Eng]. *J Enzyme Inhib Med Chem* 26:1 (2011): 98-103.

Freemont, A. J., and J. A. Hoyland. "Morphology, Mechanisms and Pathology of Musculoskeletal Ageing." [In Eng]. *J Pathol* 211:2 (2007): 252-9.

Gautieri, Alfonso, Markus J. Buehler, and Alberto Redaelli. "Deformation Rate Controls Elasticity and Unfolding Pathway of Single Tropocollagen Molecules." *Journal of the Mechanical Behavior of Biomedical Materials* 2:2 (2009): 130-37.

Huang, C., and I. V. Yannas. "Mechanochemical Studies of Enzymatic Degradation of Insoluble Collagen Fibers." [In Eng]. *J Biomed Mater Res* 11:1 (1977): 137-54.

In't Veld, P., and M. J. Stevens. "Simulation of the Mechanical Strength of a Single Collagen Molecule." [In Eng]. *Biophys J* 95:1 (2008): 33-39.

Joshi, D., R. Gupta, A. Dubey, A. Shiwalkar, P. Pathak, R. C. Gupta, V. Chauthaiwale, and C. Dutt. "Trc4186, a Novel Age-Breaker, Improves Diabetic Cardiomyopathy and Nephropathy m Ob-Zsfl Model of Type 2 Diabetes." [In Eng]. *J Cardiovasc Pharmacol* 54:1 (2009): 72-81.

Kuznetsova, N. V., McBride, D. J. and Leikin, S. "Changes in thermal stability and microunfolding pattern of collagen helix resulting from the loss of alpha2(I) chain in osteogenesis imperfecta murine." *J Mol Biol* 331 (2003): 191-200.

Maroudas, A., G. Palla, and E. Gilay. "Racemization of Aspartic Acid in Human Articular Cartilage." [In Eng]. *Connect Tissue Res* 28:3 (1992): 161-9.

Motwani, J. G., and E. J. Topol. "Aortocoronary Saphenous Vein Graft Disease: Pathogenesis, Predisposition, and Prevention." [In Eng]. *Circulation* 97: 9 (1998): 916-31.

Nabeshima, Y., E. S. Grood, A. Sakurai, and J. H. Herman. "Uniaxial Tension Inhibits Tendon Collagen Degradation by Collagenase in Vitro." [In Eng]. *J Orthop Res* 14:1 (1996): 123-30.

Ottani, V., D. Martini, M. Franchi, A. Ruggeri, and M. Raspanti. "Hierarchical Structures in Fibrillar Collagens." [In Eng]. *Micron* 33:7-8 (2002): 587-96.

Paik, D. C., L. Y. Saito, D. D. Sugirtharaj, and J. W. Holmes. "Nitrite-Induced Cross-Linking Alters Remodeling and Mechanical Properties of Collagenous Engineered Tissues." [In Eng]. *Connect Tissue Res* 47: 3 (2006): 163-76.

Pathak, P., R. Gupta, A. Chaudhari, A. Shiwalkar, A. Dubey, A. B. Mandhare, R. C. Gupta, D. Joshi, and V. Chauthaiwale. "Trc4149 a Novel Advanced Glycation End Product Breaker Improves Hemodynamic Status in Diabetic Spontaneously Hypertensive Rats." [In Eng]. *Eur J Med Res* 13:8 (2008): 388-98.

Purslow, P. P., T. J. Wess, and D. W. Hukins. "Collagen Orientation and Molecular Spacing During Creep and Stress-Relaxation in Soft Connective Tissues." [In Eng]. *J Exp Biol* 201:1 (1998): 135-42.

Puxkandl, R., I. Zizak, O. Paris, J. Keckes, W. Tesch, S. Bernstorff, P. Purslow, and P. Fratzl. "Viscoelastic Properties of Collagen: Synchrotron Radiation Investigations and Structural Model." [In Eng]. *Philos Trans R Soc Lond B Biol Sci* 357:1418 (2002): 191-7.

Rahbar, S., and J. L. Figarola. "Novel Inhibitors of Advanced Glycation Endproducts." [In Eng]. *Arch Biochem Biophys* 419:1 (2003): 63-79.

Reddy, G. K. "Glucose-Mediated in Vitro Glycation Modulates Biomechanical Integrity of the Soft Tissues but Not Hard Tissues." [In Eng]. *J Orthop Res* 21:4 (2003): 738-43.

Reddy, G. K., L. Stehno-Bittel, and C. S. Enwemeka. "Glycation-Induced Matrix Stability in the Rabbit Achilles Tendon." [In Eng]. *Arch Biochem Biophys* 399:2 (2002): 174-80.

Ruberti, J. W., and N. J. Hallab. "Strain-Controlled Enzymatic Cleavage of Collagen in Loaded Matrix." [In Eng]. *Biochem Biophys Res Commun* 336:2 (2005): 483-9.

Sasaki, N. A., M. C. Garcia-Alvarez, Q. Wang, L. Ermolenko, G. Franck, N. Nhiri, M. T. Martin, N. Audic, and P. Potier. "N-Terminal 2,3-Diaminopropionic Acid (Dap) Peptides as Efficient Methylglyoxal Scavengers to Inhibit Advanced Glycation Endproduct (Age) Formation." [In Eng]. *Bioorg Med Chem* 17:6 (2009): 2310-20.

Sell, D. R., and V. M. Monnier. "Conversion of Arginine into Ornithine by Advanced Glycation in Senescent Human Collagen and Lens Crystallins." [In Eng]. *J Biol Chem* 279:52 (2004): 54173-84.

Tanaka, S., G. Avigad, E. F. Eikenberry, and B. Brodsky. "Isolation and Partial Characterization of Collagen Chains Dimerized by Sugar-Derived Cross-Links." [In Eng]. *J Biol Chem* 263:33 (1988): 17650-7.

Tang, Yuye, Roberto Ballarini, Markus J. Buehler, and Steven J. Eppell. "Deformation Micromechanisms of Collagen Fibrils under Uniaxial Tension." *Journal of The Royal Society Interface* 7:46 (2010): 839-50.

Verzijl, N., J. DeGroot, Z. C. Ben, O. Brau-Benjamin, A. Maroudas, R. A. Bank, J. Mizrahi, et al. "Crosslinking by Advanced Glycation End Products Increases the Stiffness of the Collagen Network in Human Articular Cartilage: A Possible Mechanism through Which Age Is a Risk Factor for Osteoarthritis." [In Eng]. *Arthritis Rheum* 46:1 (2002): 114-23.

Verzijl, N., J. DeGroot, E. Oldehinkel, R. A. Bank, S. R. Thorpe, J. W. Baynes, M. T. Bayliss, et al. "Age-Related Accumulation of Maillard Reaction Products in Human Articular Cartilage Collagen." [In Eng]. *Biochem J* 350: 2 (2000): 381-7.

Verzijl, N., J. DeGroot, S. R. Thorpe, R. A. Bank, J. N. Shaw, T. J. Lyons, J. W. Bijlsma, et al. "Effect of Collagen Turnover on the Accumulation of Advanced Glycation End Products." [In Eng]. *J Biol Chem* 275:50 (2000): 39027-31.

Wyatt, K. E., J. W. Bourne, and P. A. Torzilli. "Deformation-Dependent Enzyme Mechanokinetic Cleavage of Type I Collagen." [In Eng]. *J Biomech Eng* 131:5 (2009): 051004.

Zareian, R., K. P. Church, N. Saeidi, B. P. Flynn, J. W. Beale, and J. W. Ruberti. "Probing Collagen/Enzyme Mechanochemistry in Native Tissue with Dynamic, Enzyme-Induced Creep." [In Eng]. *Langmuir* 26:12 (2010): 9917-26.

The invention claimed is:

1. A method of breaking, removing and/or eliminating advanced glycation end-product cross-links in collagen in a graft, implant, scaffold, or construct consisting of tissue isolated from a mammal and suitable for implantation into a subject for the treatment, repair or replacement of defects or injury in a biological tissue or organ, comprising incubating, prior to implantation into the subject, said graft, implant, scaffold or construct with an agent that breaks, removes, and/or eliminates advanced glycation end-product cross-links in said collagen for a time and at a temperature during which the advanced glycation end-product cross-links in said collagen in said graft, implant, scaffold, or construct are broken, removed, and/or eliminated, followed by rinsing or washing the agent from said graft, implant, scaffold or construct, wherein said agent is no longer present in the graft, implant, scaffold or construct prior to implantation of said graft, implant, scaffold or construct into the subject, and wherein said agent is selected from the group consisting of ALT-462, ALT-486, ALT-946, N-phenacylthiazolium bromide (PTB), TRC4186, TRC4149, C36 and C16.

2. The method of claim 1, wherein the graft, implant, scaffold, or construct is an autograft, an isograft, an allograft, or a xenograft.

3. The method of claim 1, wherein the biological tissue is musculoskeletal, vascular, epidermal, dermal, connective, neurological, or dental.

4. The method of claim 1, wherein the organ is skin, heart, lung esophagus, kidney, liver, or lymph glands.

5. The method of claim 1, wherein the subject is a mammal.

6. The method of claim 5, wherein the mammal is a human, a non-human primate, an ovine, a porcine, an equine, a canine, a feline, or a bovine.

7. The method of claim 1, wherein graft, implant, scaffold, or construct is incubated, prior to implantation into the subject with the agent that breaks, removes, and/or eliminates cross-links in collagen for a time of about one (1) minute to about seventy-two (72) hours.

8. The method of claim 1, wherein graft, implant, scaffold, or construct is incubated, prior to implantation into the subject with the agent that, breaks, removes, and/or eliminates cross-links in collagen for a time of about one (1) minute to about one hundred and twenty (120) minutes.

9. The method of claim 1, wherein graft, implant, scaffold, or construct is incubated, prior to implantation into the subject with the agent that, breaks, removes, and/or eliminates cross-links in collagen for a time of about four (4) to about sixteen (16) hours.

10. The method of claim 1, wherein graft, implant, scaffold, or construct is incubated, prior to implantation into the subject with the agent that, breaks, removes, inhibits and/or eliminates cross-links in collagen at a temperature of between about 4° C. and about 37° C.

* * * * *